United States Patent [19]

Theodoridis

[11] Patent Number: 4,868,321
[45] Date of Patent: Sep. 19, 1989

[54] ISOTHIOCYANATE INTERMEDIATES

[75] Inventor: George Theodoridis, Princeton, N.J.

[73] Assignee: FMC Corporation, Philadelphia, Pa.

[21] Appl. No.: 224,274

[22] Filed: Jul. 25, 1988

Related U.S. Application Data

[63] Continuation of Ser. No. 12,572, Feb. 9, 1987, abandoned, which is a continuation-in-part of Ser. No. 814,575, Dec. 26, 1985, which is a continuation-in-part of Ser. No. 671,532, Nov. 14, 1984, abandoned, which is a continuation-in-part of Ser. No. 549,334, Nov. 4, 1983, abandoned.

[51] Int. Cl.$^4$ .......................................... C07C 161/04
[52] U.S. Cl. ................................................. 558/17
[58] Field of Search ........................................ 558/17

[56] References Cited

U.S. PATENT DOCUMENTS

| | | | |
|---|---|---|---|
| 2,775,587 | 12/1957 | Fischback | 558/17 |
| 2,938,042 | 5/1960 | Stevenson et al. | 558/17 |
| 2,980,668 | 4/1961 | Stevenson et al. | 558/17 |
| 3,629,332 | 12/1971 | Harrington et al. | |
| 3,755,406 | 8/1973 | Brenneisen et al. | 558/17 |
| 3,755,605 | 8/1973 | Moore et al. | 424/321 |
| 3,865,570 | 2/1975 | George | 71/76 |
| 3,975,418 | 8/1976 | Duerr | 260/453 |
| 4,349,378 | 9/1982 | Cliff et al. | 11/103 |
| 4,404,019 | 9/1983 | Uematsu et al. | 71/92 |
| 4,427,438 | 1/1984 | Nagano et al. | 71/92 |
| 4,439,229 | 3/1984 | Swithenbank | 71/96 |
| 4,452,981 | 6/1984 | Nagano et al. | 544/236 |
| 4,552,585 | 11/1985 | Chang | 71/88 |
| 4,618,365 | 11/1986 | Covey et al. | 71/92 |

FOREIGN PATENT DOCUMENTS

| | | |
|---|---|---|
| 0011693 | 6/1980 | European Pat. Off. |
| 0077938 | 5/1983 | European Pat. Off. |
| 1421234 | 11/1965 | France .................... 558/17 |
| 160447 | 8/1983 | German Democratic Rep. |

OTHER PUBLICATIONS

O. Tsuge et al., "Reactions of Trimethylsilyl Azide with Heterocumulenes", *J. Org. Chem.*, 45, 5130 (1980).

J. M. Vandensavel et al., "Reactions of Azides with Isocyanates, Cycloadditions and Cycloreversions", *J. Org. Chem.*, 38, 675 (1973).

J. P. Horwitz et al., "The Synthesis of 1-Substituted 5(4H) Tetrazolinones", *J. Am. Chem. Soc.*, 81, 3076 (1959).

*Primary Examiner*—David B. Springer
*Attorney, Agent, or Firm*—Robert M. Kennedy; H. Robin Ertelt; Abner Sheffer

[57] ABSTRACT

Herbicidial substituted phenyl tetrazolinones in which there is a substituted sulfonylamino group at the 5-position of the phenyl ring; intermediates and processes for producing them, including intermediates which are 2,4-dihalo-5-alkylsulfonylaminophenyl isothiocyanates; and compositions containing herbicides and methods for their use.

2 Claims, No Drawings

ISOTHIOCYANATE INTERMEDIATES

This application is a continuation of application Ser. No. 012,572, filed 2/9/87, which is a continuation in part of application Ser. No. 814,575 filed Dec. 26, 1985, which is in turn a continuation in part of application Ser. No. 671,532 filed Nov. 14, 1984 (now abandoned), which is in turn a continuation in part of application Ser. No. 549,334 filed Nov. 4, 1983 (now abandoned). This application incorporates by reference the entire disclosure of said application Ser. No. 814,575 and of the corresponding published International application no. WO 85/01939 published May 9, 1985.

This application relates particularly to selective herbicidal compounds of the formula:

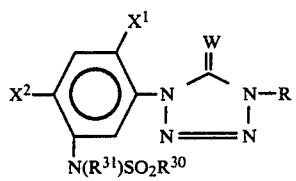

Formula I wherein $R^{30}$ may be alkyl (such as straight chain or branched chain lower alkyl, e.g. methyl, ethyl, propyl), haloalkyl (such as $CF_3$ or $CHF_2$), dialkylamino, aryl (such as phenyl, optionally substituted with one or more of: halogen such as Cl, Br or F; alkyl such as lower alkyl, e.g. methyl; alkoxy such as lower alkoxy; e.g. methoxy; cyano; cyanomethyl; nitro; amino; arylamino such as phenylamino; mono- and dialkylamino such as methylamino or dimethylamino; carboxyl; alkoxycarbonyl such as —$COOC_2H_5$; alkoxyalkyl such as alkoxymethyl of 2 to 4 carbon atoms; alkoxycarbonylalkyl such as —$CH_2COOC_2H_5$; benzyl; or hydroxy).

$R^{31}$ may be hydrogen, alkyl (e.g. straight or branched chain lower alkyl such as methyl, ethyl, propyl, isopropyl or butyl), benzyl, haloalkyl (e.g. $CHF_2$ or $CH_2CH_2CH_2F$), alkoxy (e.g. methoxy), $SO_2R^{30}$, alkynyl (such as propargyl), alkenyl (such as allyl), a group of the formula -alkylene-$SO_2R^{30}$ (in which, for example, said alkylene group (e.g. —$CH_2$—) has 1 to 4 carbon atoms, alkoxymethyl (such as methoxymethyl), cyanomethyl, carboxymethyl (including salts thereof) or alkoxycarbonylmethyl.

$R^{30}$ and $R^{31}$ together may be a divalent radical such as alkylene (e.g. of 1 to 10 carbon atoms such as methylene or 1,3-propylene).

Disclosed herein are certain acidic sulfonamides such as those in which $R^{31}$ is hydrogen. Such acidic compounds may be used in the form of their salts such as a sodium, potassium, calcium, ammonium, magnesium or mono-, di- or tri($C_1$ to $C_4$)alkyl ammonium salt. Other suitable herbicidal salts of these sulfonamides are the sulfonium or sulfoxonium salts, such as salts of bases of the formula $R''_3S(O)_n$ where $R''$ is, for instance, lower alkyl (e.g. $C_1$—$C_3$ alkyl) and n is zero or one, e.g. the trimethylsulfoxonium salt. Thus $R^{31}$ may also be a salt-forming group such as a metal (e.g. Na, K or Ca) or ammonium (e.g. $NH_4$ or lower alkyl-substituted ammonium) or sulfonium or sulfoxonium.

R may be alkyl (preferably of 1 to 6 carbon atoms), haloalkyl (preferably of 1 to 5 carbon atoms), alkoxyalkyl (preferably of 2 to 6 carbon atoms), alkylthioalkyl (preferably of 2 to 6 carbon atoms), cyanoalkyl (preferably of 1 to 5 alkyl carbon atoms), haloalkoxyalkyl (preferably of 2 to 6 carbon atoms), trifluoromethylthio, alkenyl (preferably of 2 to 5 carbon atoms), or haloalkenyl (preferably of 2 to 5 carbon atoms).

W is preferably O but may also be S.

One of $X^1$ and $X^2$ is fluorine, chlorine, or bromine and the other is fluorine, chlorine, bromine, alkyl (preferably of 1 to 6 carbon atoms) such as methyl, or haloalkyl (preferably of 1 to 5 carbon atoms) such as bromomethyl, fluoromethyl, or trifluoromethyl. When $X^1$ is fluorine, chlorine, or bromine, $X^2$ may be selected from the substituents above and nitro.

With respect to sub-genera for $X^1$ and $X^2$, $X^1$ may be fluorine, chlorine, bromine, methyl, or trifluoromethyl and $X^2$ may be fluorine, chlorine, bromine, methyl, ethyl, bromoethyl, fluoromethyl, trifluoromethyl, or nitro, one of $X^1$ and $X^2$ being fluorine, chlorine, or bromine. In a preferred embodiment, $X^1$ and $X^2$ independently will be selected from fluorine, chlorine, and bromine. In a particularly preferred embodiment $X^1$ will be chlorine, or, especially, fluorine and $X^2$ will be chlorine.

In each aspect of the invention, it is often preferable that any alkyl, alkenyl, alkynyl or alkylene moiety have less than 6 carbon atoms.

It will be understood that any alkyl, alkenyl or alkynyl moiety of the compound may be straight chain or branched chain radicals. Thus, 1-methylethyl, 2-methyl-2-propenyl, and 1-methyl-2-propynyl are branched chain examples of alkyl, alkenyl, and alkynyl radicals respectively.

A particularly effective selective herbicidal compound is compound No. 4 of Tables 1 and 2 below, especially for preemergent use on such crops as soybeans, corn, barley, wheat, rice (e.g. paddy rice), beans, peas, peanuts and potatoes. It is effective at low rates, e.g. at about 0.5 kg/ha and below, such as rates of 0.375, 0.25, 0.1 or 0.06 kg/ha and even lower, such as 0.015 kg/ha. At these low rates the compound is particularly useful in combination with other herbicides such as 2-[(2-chlorophenyl)methyl]-4,4-dimethyl-3-isoxazolidone, trifluralin (i.e. N,N-dipropyl-alpha, alpha, alpha-trifluoro-2,6-dinitro-ptoluidine), tridiphane (i.e. 2-(3,5-dichlorophenyl)- (2,2,2-trichloroethyl)oxirane), alachlor (i.e. 2-chloro-2,6'-diethyl-N-(methoxymethyl)acetanilide) or any of the following:

| | |
|---|---|
| isoproturon | bentozon |
| chlortoluron | acifluorfen-sodium |
| clopyralid | chlorpropham |
| bromoxynil | imazaquin |
| pyridate | 2,4-DB |
| bifenox | paraquat |
| chlorsulfuron | glyphosate |
| dichlofop-methyl | vernolate |
| difenzoquat | chlorimuron |
| dicamba | atrazine |
| dinoseb | cyanozine |
| triallote | simazine |
| barban | EPTC |
| 2,4-D esters | butylate |
| 2,4-D amine salts | propanil |
| terbutryne | molinate |
| flamprop-isopropyl | oxadiazon |
| propachlor | butachlor |
| metolachlor | pyrazolate |
| chloramben | thiobencarb |
| linuron | napropamide |
| trifluralin | |
| oryzalin | |
| pendimetholin | |

The pre-emergence application of the tetrazolinone herbicide may be combined with a sequential, postemergent treatment with another herbicide such as one of the known grass-controlling herbicides which show a favorable selectivity for the particular crop. Such post-emergence treatment may be made, say, one or two weeks or more (e.g. a month) after the emergence of the crop. Herbicides that may thus be applied sequentially in combination with the preemergence application of the tetrazolinone include such materials as the ethyl ester of 2-(4-((6-chloro-2-quinoxalinyl)-oxy)phenoxy)-propionic acid; sethoxydim; haloxyfopmethyl; and quinofop-ethyl.

For instance, compositions for preemergence application were formulated by mixing Aqueous Suspension A (described below) with Flowable Concentrate B (also described below) and water, the relative proportions and rates of application being such that the active ingredients were applied for weed control at rates shown in Table B, below, to a field planted with soybeans:

TABLE B

| Active Ingredient (in Kg/ha) | | |
|---|---|---|
| Mixture No. | A | B |
| 1 | 0.063 | 0.28 |
| 2 | 0.125 | 0.28 |
| 3 | 0.25 | 0.28 |
| 4 | 0.50 | 0.28 |
| 5 | 0.063 | 0.56 |
| 6 | 0.125 | 0.56 |
| 7 | 0.25 | 0.56 |
| 8 | 0.50 | 0.56 |
| 9 | 0.063 | 0.84 |
| 10 | 0.125 | 0.84 |
| 11 | 0.25 | 0.84 |
| 12 | 0.50 | 0.84 |

Here the ratio of A:B is in the range of about 0.05:1 to 2:1.

| Aqueous Suspension A | % by Wt. |
|---|---|
| Active ingredient A (Compound No. 4) | 4.92 |
| Antimicrobial agent | 0.05 |
| Foam suppressant | 0.10 |
| Surfactant C | 2.60 |
| Surfactant D | 0.40 |
| Thickener | 0.35 |
| Suspending agent | 0.45 |
| Propylene glycol (antifreeze) | 6.00 |
| Water | 85.13 |
| Total | 100.00 |

The antimicrobial agent is sodium o-phenylphenate tetrahydrate sold under the trademark and designation "Dowacide A". The foam suppressant is a water dilutable silicone emulsion sold under the trademark and designation "Dow Corning AF". Surfactant C is a nonionic paste of a condensate of ethylene oxide with a hydrophobic base formed by condensing propylene oxide with propylene glycol, sold under the trademark and designation "Pluronic P-84." Surfactant D is an anionic liquid comprising the sodium salt of a complex organic phosphate ester, sold under the trademark and designation "GAFAC LO-529." The thickener is a xantham gum sold under the trademark and designation "Kelzan-M". The suspending agent is a colloidal magnesium aluminum silicate sold under the trademark and designation "Veegum." To prepare this Suspension A, all the ingredients, except the thickener and some 4/10 of the total water, are ground together after which the thickener and the balance of the water are added.

| Flowable Concentrate B | |
|---|---|
| Active ingredient B* | 64.3% |
| Inert solvent plus minor amount of emulsifier | 35.7% |

Active ingredient B is 2- 2-chlorophenyl)-methyl-4,4-dimethyl-3-isoxazolidinone

The above-mentioned compound 4 of Tables 1 and 2 also shows very good control of broadleafed weeds in plantings of such crops as corn, wheat, barley, oats, rice and sorghum, when applied postemergently. Here rates of application in the field may be, for instance, in the range of about 30 to 250 g/ha, e.g. 125 g/ha.

Another particularly suitable compound is compound 14 of Tables 1 and 2. This is a highly selective herbicide for use with cotton or soybeans particularly for pre-emergence application at rates below about ¼ or 1/10 kg/ha (such as rates of 0.06, 0.03 or 0.015 kg/ha).

The compounds of this invention may be prepared by the use of steps generally described in the literature or in the following Examples or by methods analogous or similar thereto and within the skill of the art. In Example I below an arylamine is treated to form the corresponding aryl isocyanate whose isocyanate portion is then modified to form a tetrazolinone ring. Thereafter the benzene ring of the intermediate is nitrated, the nitro group is reduced to form an amino group, which is then treated with $R^{30}SO_2Cl$ or $(R^{30}SO_2)_2O$ to convert it to an $-N(R^{31})SO_2R$ group (e.g. by carrying out the reaction in the presence of a weak base such as pyridine or $NaHCO_3$) or to an $-N(SO_2R^{30})_2$ group. The compound having the $-N(SO_2R^{30})_2$ group may then be treated (as with a base such as NaOH) to form the corresponding $-NR^{31}SO_3R^{30}$ group, where $R^{31}$ is a salt-forming group (e.g. Na); this may then be treated with an acid to form the corresponding (acidic) $-NH-SO_2R^{30}$ group. In one embodiment, subsequent alkylation (as by treatment with the appropriate alkyl iodide as in Example VI) forms the corresponding

group. When the reaction sequence involves $R^{30}SO_2Cl$ treatment of an intermediate having hydrogen on the 4-nitrogen of the tetrazolinone ring, that hydrogen may also be replaced, during such treatment, by $R^{30}SO_2-$ to form an intermediate (such as a compound which has three $R^{30}SO_2-$ groups) from which the $R^{30}SO_2-$ group on said 4-nitrogen may be removed readily by the treatment with the base, after which the appropriate R group may be substituted on said 4-nitrogen.

The sequence of steps may be changed. For instance one may start with a nitroaniline, such as 3-nitroaniline or 2-fluoro-5-nitroaniline, then make the corresponding isocyanate and convert the isocyanate group to a tetrazolinone ring (as by treatment with trimethylsilylazide) and then reduce the nitro group and substitute an R group on N-4 of the tetrazolinone ring, in either order. Thereafter the amino group may be converted to a $N(R^{31})$ group, after which the compound may be halogenated (as with $SO_2Cl_2$ in dioxane) to place a halogen at the 4-position of the benzene ring (or, when the intermediate being halogenated does not yet have the halogen on its 2-position, this halogenation may place halogen atoms at both the 2- and 4-positions of the benzene ring). Thus the following series of successive intermediates may be prepared from 2-fluoro-5-nitroaniline:
2-fluoro-5-nitrophenyl isocyanate;
1-(2-fluoro-5-nitrophenyl)-1,4-dihydro-5H-tetrazol-5-one (m.p. 124°–125° C.);
1-(2-fluoro-5-aminophenyl)-1,4-dihydro-5H-tetrazol-5-one (m.p. 169°–171° C.); or 1-(2-fluoro-5-nitrophenyl)-1,4-dihydro-4-(3-fluoropropyl)-5H-tetrazol-5-one;
1-(2-fluoro-5-aminophenyl)-1,4-dihydro-4-(3-fluoropropyl)-5H-tetrazol-5-one (an oil);
1-[2-fluoro-5-(bis(N-ethylsulfonyl)amino)phenyl]-1,4-dihydro-4-(3-fluoropropyl)-5H-tetrazol-5-one;
1-[2-fluoro-5-(ethylsulfonylamino)phenyl]-1,4-dihydro-4-(3-fluoropropyl)-5H-tetrazol-5-one.

When the starting material is 3-nitrophenylaniline, the corresponding intermediates without the 2-fluoro substituent may be formed, and the last intermediate may then be treated to place the halogens at its 2- and 4-positions of its benzene ring.

One may also start with, for example 2-fluoroaniline and, by a series of reactions, convert the amino group to a tetrazolinone group (either through formation of the isocyanate as in Example 1 or through the formation of a tetrazolinethione as discussed below) so as to form the 1-(2-fluorophenyl)-1,4-dihydro-5H-tetrazol-5-one, which (as by substitution of an R group for the H on the N-4 of the tetrazolinone ring) is then converted to, for instance, 1-(2-fluorophenyl)-1,4-dihydro-4-(3-fluorophenyl)-5H-tetrazol-5-one. This may be chlorinated to form the compound of Example I Step C, below.

Alternatively, one may start with 4-fluoronitrobenzene and, by a series of reactions (e.g. by reducing the $NO_2$ group to an amino group and then nitrating to form 3-nitro-4-fluoroaniline, followed by treatment with the alkylsulfonyl halide) to form 2-fluoro-5-bis(N-ethylsulfonyl)aminonitrobenzene, which is then reduced to form 2-fluoro-5-bis(N-ethylsulfonyl)amino aniline and then converted to the corresponding 1-[2-fluoro-5-bis(N-ethylsulfonyl)aminophenyl]1,4-dihydro-5H-tetrazol-5-one, which may then be treated to substitute an R group on the N-4 of the tetrazolinone ring to form, for instance, the compound of Example II. The conversion of the amino group to the tetrazolinone ring may be effected through formation of the isocyanate in the manner illustrated in Example I (thus forming 2-fluoro-5-(bis(N-ethylsulfonyl)amino)phenyl isocyanate) or through intermediate formation of a tetrazolinethione as discussed below.

From another starting material, 2-fluoro-5-nitroaniline, one may produce (either through the previously mentioned 2-fluoro-5-nitrophenyl isocyanate or through a corresponding tetrazolinethione as discussed below) the previously mentioned 1-(2-fluoro-5-aminophenyl)-1,4-dihydro-5H-tetrazol-5-one. In another route from the same 2-fluoro-5-nitroaniline starting material, one may (as illustrated in Example VIII) acetylate the $NH_2$ to protect it; then reduce the nitro group to form an amino group; chlorinate and treat with alkylsulfonyl chloride in any order (to form, e.g., 2-fluoro-4-chloro-5-(ethylsulfonylamino)acetanilide); then hydrolyze off the acetyl group to form 2-fluoro-4-chloro-5-(ethylsulfonylamino)aniline, whose free $NH_2$ group may then be converted (e.g. through formation of an isocyanate or a tetrazolinethione as discussed below) to a tetrazolinone ring, thus forming 1-[2-fluoro-4-chloro-5-(ethylsulfonylamino)phenyl]-1,4-dihydro-5H-tetrazol-5-one.

Similarly, starting with 2-fluoro-4-chloro-5-nitroaniline one may acetylate to form 2-fluoro-4-chloro-5-nitroacetailide (m.p. 138°–140° C.); reduce to form 2-fluoro-4-chloro-5-aminoacetanilide (m.p. 117°–120° C., dec.) and then alkylsulfonate to form, e.g. 2-fluoro-4-chloro-5-bis(N-ethylsulfonyl)aminoacetanilide (m.p. 218°–219° C.) and/or 2-fluoro-4-chloro-5-(N-ethylsulfonylamino)acetanilide.

Instead of using the isocyanate route for the production of the aryl tetrazolinone from the corresponding aryl amine (as illustrated in Example 1 Steps A and B), one may react the aryl amine so as to form an aryl tetrazolinethione (with intermediate formation of an aryl isothiocyanate). The aryl tetrazolinethione may then be converted to the corresponding aryl tetrazolinone as by the method illustrated in Example VII below in which the aryl tetrazolinethione is reacted with a base and an alkyl halide to produce an aryl tetrazolyl alkyl sulfide, which is then treated with a base to form the aryl tetrazolinethione. To form the aryl tetrazolinethione from the arylamine one may react the latter with thiophosgene to form the aryl isothiocyanate and then react that isothiocyanate with an azide (e.g. with sodium azide in water at room temperature). Alternatively one may react the aryl amine with carbon disulfide (forming an intermediate dithiocarbamate) and sodium azide to obtain the aryl tetrazolinethione; during these reactions an intermediate aryl isothiocyanate is formed. By these procedures intermediates such as the following may be produced:
sodium N-(2-fluoro-5-nitrophenyl)dithiocarbamate;
2-fluoro-5-nitrophenyl isothiocyanate;
1-(2-fluoro-5-nitrophenyl)-1,4-dihydro-5H-tetrazol-5-thione and its sodium salt;
sodium N-(4-chloro-2-fluorophenyl)dithiocarbamate;
4-chloro-2-fluorophenyl isothiocyanate;
1-(4-chloro-2-fluorophenyl)-1,4-dihydro-5H-tetrazol-5-thione and its sodium salt;
sodium N-(4-chloro-2-fluoro-5-(ethylsulfonylamino)phenyl dithiocarbamate;
2-fluoro-4-chloro-5(ethylsulfonylamino)phenyl isothiocyanate;
1-[2-fluoro-4-chloro-5-(ethylsulfonylamino)phenyl]-5H-tetrazol-5-thione and its sodium salt;
sodium N-[2-fluoro-5-bis(N-ethylsulfonyl)aminophenyl]dithiocarbamate;
2-fluoro-5-bis(N-ethylsulfonyl)aminophenyl isothiocyanate;
1-[2-fluoro-5-(bis(N-ethylsulfonyl)amino)phenyl]5H-tetrazol-5-thione and its sodium salt.

It will be understood that other salts may be made and used instead of the sodium salts (of, say, the thione or the dithiocarbamate), e.g. salts of other alkali metals or onium salts (e.g. triethylammonium salt).

The reaction with $R^{30}SO_2Cl$ or $(R^{30}SO_2)_2O$ may be effected at, for instance, a temperature below 60° C. such as −10° to 50° C. in the presence of a suitable base and an inert solvent.

The halogenation reaction with chlorine or bromine may be effected at, for instance, a temperature of about 20° to 150° C.

The introduction of the fluoropropyl group may be effected at, for instance, about 20° to 130° C., preferably by reacting fluoropropyl-$X^4$ wherein $X^4$ is a leaving group, e.g. 1-bromo-3-fluoropropane, 1-chloro-3-fluoropropane or 3-fluoropropyl methane sulfonate in the presence of a suitable base (e.g. NaOH) and a suitable solvent (e.g. N,N-dimethylformamide or acetone).

The types of intermediates described herein include, inter alia, those of the following Formulas II-IX in which $X^1$, $X^2$, R, $R^{30}$ and $R^{31}$ are as described above, M is an alkali metal or onium ion and M' is H or M,

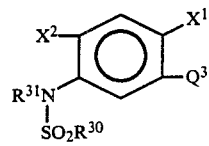
Formula II where $Q^3$ is $NO_2$, $NH_2$, —NCS, —NCO, 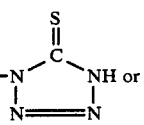 or

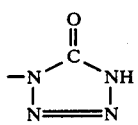

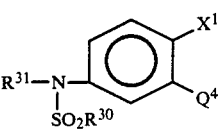
Formula III where $Q^4$ is $NO_2$, $NH_2$, NCS, NCO, NH—C(S)SM,

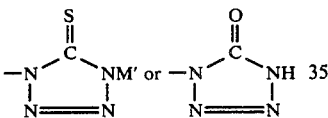

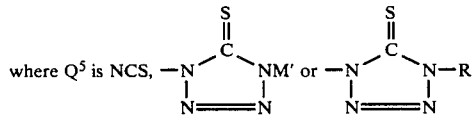
Formula IV where $Q^5$ is NCS, 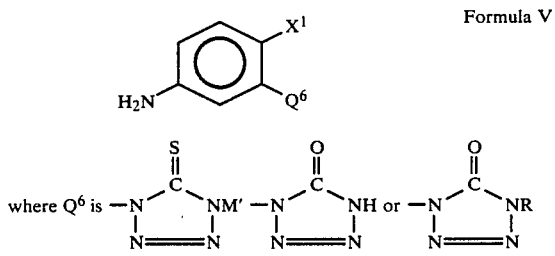

Formula V

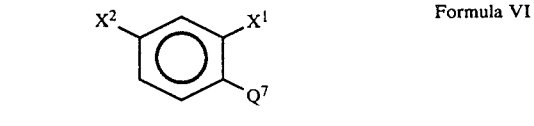

where $Q^6$ is 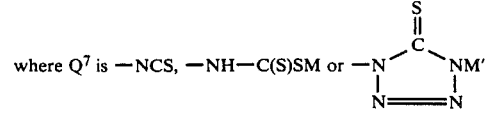

Formula VI where $Q^7$ is —NCS, —NH—C(S)SM or

M is alkali metal or onium ion and M' is H or M.

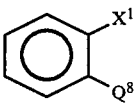
Formula VII where $Q^8$ is

Formula VIII

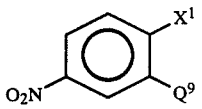

where $Q^9$ is

Formula IX

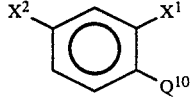

where $Q^{10}$ is —NCO or

In the above Formulas II-IX, $X^1$ is preferably F or Cl, most preferably F, $X^2$ is preferably Cl but may also be Br and R is preferably —$CH_2CH_2CH_2F$.

The Examples below illustrate the preparation of compounds in which Z (in Formula I above) is $N(R^{31})SO_2R^{30}$. Compounds of this type are listed in Table 1, physical properties thereof are given in Table 2 and herbicidal data therefor are given in Tables 3 and 4.

EXAMPLE I

SYNTHESIS OF 1-(5-AMINO-4-CHLORO-2-FLUOROPHENYL)-1,4-DIHYDRO-4-(3-FLUOROPROPYL)-5H-TETRAZOL-5-ONE AS AN INTERMEDIATE

Step A

Synthesis of 4-chloro-2-fluorophenyl isocyanate as an intermediate

To a stirred solution of 20.0 g (0.13 mole) of 4-chloro-2-fluoroaniline in 250 ml of toluene was added dropwise a solution of 17.2 ml (0.13 mole) of trichloromethyl chloroformate in 40 ml of toluene. Upon completion of addition the reaction mixture was heated to reflux where it stirred for 16 hours. The solvent was separated from the reaction mixture by distillation to yield 21.8 g of 4-chloro-2-fluorophenyl isocyanate as an oil. The reaction was repeated several times.

Step B

Synthesis of
1-(4-chloro-2-fluorophenyl)-1,4-dihydro-5H-tetrazol-5-one as an intermediate A stirred solution of 17.1 g (0.10 mole) of 4-chloro-2-fluorophenyl isocyanate and 20.0 g (0.17 mole) of azidotrimethylsilane was heated under reflux for 16 hours. The reaction mixture was cooled to ambient temperature and 60 ml of toluene and 100 ml of water were added. The mixture was allowed to stand for two hours and the resultant solid collected by filtration. The filter cake was washed with petroleum ether to yield 14.5 g of 1-(4-chloro-2-fluorophenyl-1,4-dihydro-5H-tetrazol-5-one; m.p. 185°–187° C. The reaction was repeated several times.

Step C

Synthesis of
1-(4-chloro-2-fluorophenyl)-1,4dihydro-4-(3-fluoropropyl)-5H-tetrazol-5-one as an intermediate A stirred solution of 4.7 g (0.022 mole) of 1-(4-chloro-2-fluorophenyl)-1,4-dihydro-5H-tetrazol-5-one, 4.0 g (0.028 mole) of 3-fluoropropyl bromide and 4.0 g (0.028 mole) of potassium carbonate in 60 ml of dimethylformamide was heated at 60° C. for 16 hours. The reaction mixture was poured into water and the mixture extracted with diethyl ether. The combined ether extract was dried with magnesium sulfate and filtered. The filtrate was concentrated under reduced pressure to a residue. The residue was dissolved in methylene chloride and passed through a pad of silica gel. The eluate was concentrated under reduced pressure to yield 3.5 g of 1-(4-chloro-2-fluorophenyl)-1,4-dihydro-4-(3-fluoropropyl)-5H-tetrazol-5-one; m.p. 62°–63° C. The reaction was repeated several times.

Step D

Synthesis of
1-(4-chloro-2-fluoro-5-nitrophenyl)-1,4-dihydro-4-(3-fluoropropyl)-5H-tetrazol-5-one as an intermediate To a stirred solution of 3.1 g (0.011 mole) of 1-(4-chloro-2-fluorophenyl)-1,4-dihydro-4-(3-fluoropropyl)-5H-tetrazol-5-one in 5 ml of concentrated sulfuric acid was added dropwise 0.9 ml (0.011 mole) of 70% nitric acid. Upon completion of addition the reaction mixture was stirred for two hours at ambient temperature then was poured into ice-water. The mixture was extracted with diethyl ether. The combined extracts were dried with magnesium sulfate and filtered. The filtrate was concentrated under reduced pressure to a residue. The residue was dissolved in methylene chloride and passed through a pad of silica gel. The eluate was concentrated under reduced pressure to yield 2.8 g of 1-(4-chloro-2-fluoro-5-nitrophenyl-1,4-dihydro-4-(3-fluoropropyl)-5H-tetrazol-5-one; m.p. 80°–81° C. The reaction was repeated several times.

Step E

Synthesis of
1-(5-amino-4-chloro-2-fluorophenyl)-1,4-dihydro-4-(3-fluoropropyl)-5H-tetrazol-5-one as an intermediate To a 500 ml Parr hydrogenation bottle was added 0.2 g of platinum oxide, 200 ml of ethanol, then 14.0 g (0.014 mole) of 1-(4-chloro-2-fluoro-5-nitrophenyl)-1,4-dihydro-4-(3-fluoropropyl)-5H-tetrazol-5-one. The bottle was placed in a Parr hydrogenator and the reaction mixture hydrogenated until the theoretical amount of hydrogen was taken up. The bottle was removed from the hydrogenator and the reaction mixture filtered. The filtrate was concentrated under reduced pressure to a residue. The residue was dissolved in methylene chloride and subjected to column chromatography on silica gel. The appropriate fractions were combined and concentrated under reduced pressure to yield 10.0 g of 1-(5-amino-4-chloro-2-fluorophenyl)-1,4-dihydro-4-(3-fluoropropyl)-5H-tetrazol-5-one; m.p. 84°–°86° C. The reaction was repeated several times.

EXAMPLE II

SYNTHESIS OF
1-[4-CHLORO-2-FLUORO-5-[BIS(N-ETHYLSULFONYL)AMINO]PHENYL]-1,4-DIHYDRO-4-(3-FLUOROPROPYL)-5H-TETRAZOL-5-ONE

To a stirred solution of 1.0 g (0.0035 mole) of 1-(5-amino-4-chloro-2-fluorophenyl)-1,4-dihydro-4-(3-fluoropropyl)-5H-tetrazol-5-one (prepared as in Example I) in 20 ml of methylene chloride was slowly added 0.7 g (0.007 mole) of triethylamine. The reaction mixture was cooled to 10° C. and 0.9 g (0.007 mole) of ethanesulfonyl chloride was added dropwise. Upon completion of addition the reaction mixture was allowed to warm to ambient temperature where it stirred for 16 hours. The reaction mixture was poured into ice-water and the organic layer separated. The organic layer was concentrated under reduced pressure to a residue. The residue was dissolved in methylene chloride and subjected to column chromatography on silica gel. The appropriate fractions were combined and concentrated under reduced pressure to yield 0.56 g of 1-[4-chloro-2-fluoro-5-[bis(N-ethylsulfonylamino]phenyl]-1,4-dihydro-4-(3-fluoropropyl)-5H-tetrazol-5-one; m.p. 127°–129° C.

The nmr spectrum was consistent with the proposed structure.

EXAMPLE III

SYNTHESIS OF
1-[4-CHLORO-2-FLUORO-5-(ETHYLSULFONYLAMINO)PHENYL]-1,4-DIHYDRO-4-(3-FLUOROPROPYL)-5H-TETRAZOL-5-ONE

To a stirred solution of 7.9 g (0.017 mole) of 1-[4-chloro-2-fluoro-5-[bis(N-ethylsulfonyl)amino]phenyl]-1,4-dihydro-4-(3-fluoropropyl)-5H-tetrazol-5-one (prepared as in Example II) in 100 ml of ethanol was added dropwise a solution of 1.3 g (0.033 mole) of sodium hydroxide in 6 ml of water. Upon completion of addition the reaction mixture stirred for 10 minutes and 100 ml of water was added. The mixture was neutralized with concentrated hydrochloric acid and the resultant solid collected by filtration. The solid was dried to yield 5.0 g of 1-[4-chloro-2-fluoro-5-(ethylsulfonylamino)-phenyl]-1,4-dihydro-4-(3-fluoropropyl)-5H-tetrazol-5-one; m.p. 84°–85° C.

The nmr spectrum was consistent with the proposed structure.

EXAMPLE IV

SYNTHESIS OF 1-[4-BROMO-2-FLUORO-5-[BIS(N-METHYLSULFONYL)AMINO]PHENYL]-1,4-DIHYDRO-4-(3-FLUOROPROPYL)-5H-TETRAZOL-5-ONE

This compound was prepared by a method analogous to that of Example II using 1.0 g (0.003 mole) of 1-(5-amino-4-bromo-2-fluorophenyl)-1,4-dihydro-4-(3-fluoropropyl)-5H-tetrazol-5-one (prepared as in Example I), 0.69 g (0.006 mole) of methanesulfonyl chloride, and 0.61 g (0.006 mole) of triethylamine in 20 ml of methylene chloride. The yield of 1-[4-bromo-2-fluoro--5-bis(N-methylsulfonyl)aminophenyl]-1,4-dihydro-4(3-fluoropropyl)-5H-tetrazol-5-one was 0.6 g; m.p. 143°–144° C.

The nmr spectrum was consistent with the proposed structure.

EXAMPLE V

SYNTHESIS OF 1-[4-CHLORO-2-FLUORO-5-(N-TRIFLUOROMETHYLSULFONYLAMINO)PHENYL]-1,4-DIHYDRO-4-(3-FLUOROPROPYL)-5H-TETRAZOL-5-ONE POTASSIUM SALT

Step A

Synthesis of 1-[4-Chloro-2-fluoro-5-(N-trifluoromethylsulfonylamino)phenyl]-1,4-dihydro-4-(3-fluoropropyl)-5H-tetrazol-5-one To a stirred solution of 1.0 g (0.0034 mole) of 1-(5-amino-4-chloro-2-fluorophenyl)-1,4-dihydro-4-(3-fluoropropyl)-5H-tetrazol-5-one in 30 ml of methylene chloride was added 0.20 g (0.0017 mole) of 4-(N,N-dimethyl)aminopyridine, 0.50 g (0.0017 mole) of trifluoromethylsulfonyl anhydride, and an additional 0.20 g (0.0017 mole) of 4-(N,N-dimethyl)aminopyridine. This mixture was stirred at room temperature for 0.5 hour. The resultant solution was extracted with 100 ml of a dilute, aqueous, sodium hydroxide solution. The extract was washed with 50 ml of methylene chloride and was neutralized with concentrated hydrochloric acid. This aqueous solution was extracted several times with ethyl acetate and the extracts were combined. The combined extract was dried over anhydrous sodium sulfate and filtered. The filtrate was evaporated under reduced pressure to leave a thick oil. This oil was purified by column chromatography on silica gel, eluted with methylene chloride'acetone (95:5) to yield 1.0 g of 1-[4-chloro-2-fluoro-5-(N-trifluoromethylsulfonylamino)-phenyl]-1,4-dihydro-4-(3-fluoropropyl-5H-tetrazol-5-one as a solid, m.p. 111°–113° C.

The ir and nmr spectra were consistent with the proposed structure.

Step B

1-[4-Chloro-2-fluoro-5-(N-trifluoromethyl sulfonylamino)phenyl]-1,4-dihydro-4-(3-fluoropropyl)-5H-tetrazol-5-one potassium salt A mixture of 0.42 g (0.0010 mole) of 1-[4-chloro-2-fluoro-5-(N-trifluoromethylsulfonylamino)phenyl]-1,4-dihydro-4-(3-fluoropropyl)-5H-tetrazol-5-one and 0.11 g (0.0010 mole) of potassium tert-butoxide in 10 ml of tetrahydrofuran was stirred at room temperature for approximately 30 minutes. The reaction mixture was filtered and the filtrate was evaporated under reduced pressure to yield 0.30 g of 1-[4-chloro-2-fluoro-5-(N-trifluoromethylsulfonylamino)phenyl]-1,4-dihydro-4-(3-fluoropropyl)-5H-tetrazol-5-one potassium salt as a solid, m.p. 158°–178° C.

EXAMPLE VI

1-[4-CHLORO-2-FLUORO-5-[(N-ETHYLSULFONYL-N-PROPYL)AMINO]PHENYL]-1,4-DIHYDRO-4-(3-FLUOROPROPYL)-5H-TETRAZOL-5-ONE

To a stirred mixture of sodium hydride (0.20 g of a 50% dispersion in mineral oil) in 10 ml of dimethylformamide was added 1.0 g (0.0026 mole) of 1-[4-chloro-2-fluoro-5-(ethylsulfonylamino)phenyl]-1,4-dihydro-4-(3-fluoropropyl)-5H-tetrazol-5-one (prepared as in Example III). The reaction mixture was stirred for 15 minutes and 0.5 g (0.003 mole) of 1-iodopropane was added. This mixture was stirred at room temperature for approximately 18 hours. The mixture was diluted with diethyl ether and washed in succession with an aqueous, 10% sodium hydroxide solution and an aqueous, saturated sodium chloride solution. The washed organic phase was dried over anhydrous magnesium sulfate and filtered. The filtrate was evaporated under reduced pressure to leave an oily residue. This residue was purified by column chromatography on silica gel, eluted with ethyl acetate:n-heptane (50:50), to yield 1.0 g of 1-[4-chloro-2-fluoro-5-[(N-ethylsulfonyl-N-propyl)amino]phenyl]-1,4-dihydro-4-(3-fluoropropyl)-5H-tetrazol-5-one as an oil.

The nmr and ir spectra were consistent with the proposed structure.

EXAMPLE VII

1-(4-CHLORO-2-FLUOROPHENYL)-1,4-DIHYDRO-5H-TETRAZOL-5-ONE

Step A

Triethylammonium salt of 4-chloro-2-fluorophenyl dithiocarbamic acid

A solution of 30.0 g (0.206 mole) of 4-chloro-2-fluoroaniline and 30 ml (0.215 mole) of triethylamine in 90 ml of carbon disulfide was stirred at room temperature for 22 hours, resulting in a thick suspension. The reaction mixture was filtered. The filter cake was washed with diethyl ether to yield 56.1 g of the triethylammonium salt of 4-chloro-2-fluorophenyl dithiocarbamic acid as a yellow solid.

The nmr spectrum was consistent with the proposed structure.

Step B 1-(4-Chloro-2-fluorophenyl)-1,4-dihydro-5H-tetrazol-5-thione

A stirred mixture of 5.0 g (0.016 mole) of the triethylammonium salt of 4-chloro-2-fluorophenyl dithiocarbamic acid, 0.62 g (0.016 mole) of sodium hydroxide, and 4.0 g (0.062 mole) of sodium azide in 10 ml of water was heated at reflux for three hours. The mixture was cooled to room temperature and was acidified with concentrated hydrochloric acid. A precipitate formed and was collected by filtration. The filter cake was washed with water and was dried to yield 3.2 g of 1-(4-chloro-2-fluorophenyl)-1,4-dihydro-5H-tetrazol-5-thione, m.p. 128° C.

The nmr spectrum was consistent with the proposed structure.

Step C

[1-(4-Chloro-2-fluorophenyl)-1H-tetrazol-5-yl] ethyl sulfide

A solution of 1.75 g (0.0076 mole) of 1-(4-chloro-2-fluorophenyl)-1,4-dihydro-5H-tetrazol-5-thione, 0.57 ml (0.0076 mole) of bromoethane, and 1.6 g (0.012 mole) of potassium carbonate in 8 ml of acetone was stirred at room temperature for seven hours. The solvent was evaporated from the reaction mixture under reduced pressure leaving a residue. This residue was dissolved in diethyl ether and the organic solution was washed with water. The washed organic phase was dried over anhydrous magnesium sulfate and filtered. The filtrate was evaporated under reduced pressure to yield 1.6 g of (1-(4-chloro-2-fluorophenyl)-1H-tetrazol-5-yl) ethyl sulfide as a solid, m.p. 76°-79° C.

The nmr spectrum was consistent with the proposed structure.

Step D 1-(4-Chloro-2-fluorophenyl)-1,4-dihydro-5H-tetrazol-5-one

To a stirred solution of 0.12 g (0.0052 mole) of sodium in 16 ml of ethanol was added 1.2 g (0.0046 mole) of (1-(4-chloro-2-fluorophenyl)-1H-tetrazol-5-yl)ethyl sulfide. The resultant solution was heated at reflux for six hours. The reaction mixture was cooled and the solvent was evaporated under reduced pressure leaving a residue. This residue was dissolved in 40 ml of water and the aqueous solution was washed with diethyl ether. The aqueous phase was acidified with concentrated hydrochloric acid forming a precipitate. The precipitate was collected by filtration and dried to yield 0.55 g of 1-(4-chloro-2-fluorophenyl)-1,4-dihydro-5H-tetrazol-5-one as a solid, m.p. 194° C.

EXAMPLE VIII

4-CHLORO-5-(N-ETHYLSULFONYLAMINO)-2-FLUOROPHENYL ISOTHIOCYANATE

Step A

2-Fluoro-5-Nitroacetanilide

To a stirred solution of 18.0 g (0.11 mole) of 2-fluoro-5-nitroaniline in 100 ml of dioxane was added 15.3 g (0.15 mole) of acetic anhydride. The reaction mixture was heated at reflux for two hours. The solvent was removed from the mixture by distillation under reduced pressure leaving a solid residue. This residue was stirred in 25 ml of methylene chloride and filtered. The filter cake was dried to yield 20.5 g of 2-fluoro-5-nitroacetanilide, m.p. 177°-178° C.

Step B

5-Amino-2-fluoroacetanilide

Hydrogenation of 20.0 g (0.10 mole) of 2-fluoro-5-nitroacetanilide with a catalytic amount (0.3 g) of platinum oxide in 200 ml of an ethanol/ethylacetate (80/20) solution yielded 16.0 g of 5-amino-2-fluoroacetanilide as a solid.

Step C

2-Fluoro-5-bis(N-ethylsulfonylamino)-acetanilide

To a stirred mixture of 15.4 g (0.091 mole) of 5-amino-2-fluoroacetanilide in 75 ml of methylene chloride was added 18.5 g (0.183 mole) of triethylamine. To this mixture was added slowly 23.5 g (0.183 mole) of ethyl sulfonyl chloride. The resultant mixture was stirred at room temperature for approximately 18 hours. The reaction mixture was passed through a column of silica gel, eluting with methylene chloride, to yield 12.0 g of 2-fluoro-5-bis(N-ethylsulfonylamino)acetanilide.

Steps A-C were repeated to prepare additional 2-fluoro-5-bis(N-ethylsulfonylamino)acetanilide.

Step D

2-Fluoro-5-(N-ethylsulfonylamino)-acetanilide

To a stirred solution of 27.0 g (0.077 mole) of 2-fluoro-5-bis(N-ethylsulfonylamino)acetanilide in 100 ml of dioxane was added a solution of sodium hydroxide (5.65 g, 0.0141 mole) in 20 ml of water. Approximately 100 ml of water was added and the resultant solution was stirred at room temperature for about 15 minutes. The dioxane solvent was removed from the solution by extraction with diethyl ether. The remaining aqueous phase was acidified with concentrated hydrochloric acid forming a precipitate. The precipitate was collected by filtration and dried to yield 14.8 g of 2-fluoro-5-(N-ethylsulfonylamino)acetanilide, m.p. 175.5°-177° C. Additional product (1.9 g) was collected by extracting the filtrate with ethyl acetate and evaporating the extract after drying over anhydrous magnesium sulfate.

The nmr and ir spectra were consistent with the proposed structure.

Step E

4-Chloro-2-fluoro-5-(N-ethylsulfonylamino)-acetanilide

To a stirred solution of 8.0 g (0.031 mole) of 2-fluoro-5-(N-ethylsulfonylamino)acetanilide in 200 ml of dioxane was added slowly 2.5 ml (0.031 mole) of sulfuryl chloride. This mixture was heated at 80° C. for two days. The mixture was poured into ice water and the mixture was extracted with ethyl acetate. The extract was dried over anhydrous magnesium sulfate and filtered. The filtrate was evaporated under reduced pressure to yield 8.1 g of 4-chloro-2-fluoro-5-(N-ethylsulfonylamino)acetanilide.

Step F

4-Chloro-2-fluoro-5-(N-ethylsulfonylamino)-aniline

A stirred mixture of 2.0 g (0.0068 mole) of 4-chloro-2-fluoro-5-(N-ethylsulfonylamino)acetanilide and 0.84 g (0.020 mole) of sodium hydroxide in 100 ml of water was heated at reflux for approximately 18 hours. The reaction mixture was cooled and neutralized with concentrated hydrochloric acid. The neutralized mixture was extracted with ethylacetate. The extract was washed with an aqueous, saturated sodium chloride solution. The washed extract was dried over anhydrous magnesium sulfate and filtered. The filtrate was evaporated under reduced pressure to yield 2.7 g of 4-chloro-2-fluoro-5-(N-ethylsulfonylamino)aniline as a solid.

The nmr was consistent with the proposed structure.

Step G

4-Chloro-5-(N-ethylsulfonylamino)-2-fluorophenyl isothiocyanate

Under a dry nitrogen atmosphere 0.84 ml (0.011 mole) of thiophosgene was added to a stirred solution of 2.8 g (0.011 mole) of 4-chloro-2-fluoro-5-(N-ethylsulfonylamino)aniline in 250 ml of chloroform. To this mixture was added dropwise 1.6 g (0.012 mole) of triethylamine. The resultant mixture was stirred at room temperature for approximately 18 hours. The solvent was removed from the mixture by evaporation under reduced pressure leaving an oily residue. This residue was purified by column chromatography on silica gel, eluting with methylene chloride/hexane (60/40) followed by methylene chloride, to yield 1.6 g of 4-chloro-5-(N-ethylsulfonylamino)-2-fluorophenyl isothiocyanate as a solid, m.p. 104°–105° C.

The nmr and ir spectra were consistent with the proposed structure.

The herbicidal data in the following Tables 3 and 4 was obtained in the manner described in PCT published application no. WO 85/01939, previously mentioned, usually employing solutions of the herbicidal compound in 50/50 acetone/water mixtures. In those tables, the test compounds are identified by numbers which correspond to those in Table 1, "kg/ha" is kilograms per hectare, and "% C" is percent control.

In addition, tests of the effectiveness of weed control of paddy rice were done in pots containing clay loam paddy soil under water maintained at a depth of 3 cm. In one test tubers of narrowleaf arrowhead (*Sagittaria pymaea*) and rhizomes of flatsedge (*Cyperus serotinus*) were planted in pots at depth of 2 cm and 0.5 cm respectively, rice seedlings of 2.2 leaf state were transplanted in depth of 2 cm and 0 cm and a controlled amount of a 10% wp (wettable powder) formulation of the herbicidal compound in water was dropped into the water over the soil at 1 day and 11 days, respectively, after transplanting. In another test, seeds of various weed species (including barnyardgrass, *Echinochoa crus-galli;* small flower umbrellaplant, *Cyperus difformis;* bulrush, *Scripus juncoides;* Japanese ducksalad, *Monochoria vaginalis;* annual broadleaf weeds; and narrowleaf waterplantain, *Alisma canaliculatium*) were sown on the surface of the soil and the same (1 day and 11 day) herbicide applications were made. In tests of compound 4 (of Table 1 below) very high activity against weeds of wide spectrum were shown for both the 1 day and 11 day treatments at rates of e.g., about 0.06 kg/ha or less, while there was selectivity favorable to rice transplanted at a depth of 2 cm.

Herbicidal data at selected application rates are given for various compounds of the invention in the tables below. The test compounds are identified in the tables of herbicidal data below by numbers which correspond to those used above in those tables.

"kg/ha" is kilograms per hectare.

For herbicidal application, the active compounds are formulated into herbicidal compositions by admixture in herbicidally effective amounts with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application.

These herbicidal compositions may be applied either as water-diluted sprays, or dusts, or granules (e.g. for paddy rice) in the areas in which suppression of vegetation is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the herbicidal compound and 99.0 parts of talc.

Wettable powders, also useful formulations for both pre- and postemergence herbicides, are in the form of finely divided particles which disperse readily in water or other dispersant. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5–80% of active ingredient, depending on the absorbency of the carrier, and usually also contain a small amount of a wetting, dispersing or emulsifying agent to facilitate dispersion. For example, a useful wettable powder formulation contains 80.8 parts of the herbicidal compound, 17.9 parts of Palmetto clay, and 1.0 part of sodium lignosulfonate and 0.3 part of sulfonated aliphatic polyester as wetting agents. Other wettable power formulations are:

| Component: | % by Wt. |
|---|---|
| Active ingredient | 40.00 |
| Sodium ligninsulfonate | 20.00 |
| Attapulgite clay | 40.00 |
| Total | 100.00 |
| Active ingredient | 90.00 |
| Dioctyl sodium sulfosuccinate | 0.10 |
| Synthetic fine silica | 9.90 |
| Total | 100.00 |
| Active ingredient | 20.00 |
| Sodium alkylnaphthalenesulfonate | 4.00 |
| Sodium ligninsulfonate | 4.00 |
| Low viscosity methyl cellulose | 3.00 |
| Attapulgite clay | 69.00 |
| Total | 100.00 |
| Active ingredient | 25.00 |
| Base: | 75.00 |
| 96% hydrated aluminum magnesium silicate | |
| 2% powdered sodium lignosulfonate | |
| 2% powdered anionic sodium alkyl-naphthalenesulfonate | |
| Total | 100.00 |

Frequently, additional wetting agent and/or oil will be added to the tank-mix for postemergence application to facilitate dispersion on the foliage and absorption by the plant.

Other useful formulations for herbicidal applications are emulsifiable concentrates (ECs) which are homogeneous liquid or paste compositions dispersible in water or other dispersant, and may consist entirely of the herbicidal compound and a liquid or solid emulsifying agent, or may also contain a liquid carrier, such as xylene, heavy aromatic naphthas, isophorone, or other non-volatile organic solvent. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the herbicidal composition.

The following are specific examples of emulsifiable concentrate formulations:

| Component: | % by Wt |
|---|---|
| Active ingredient | 53.01 |
| Calcium dodacylbenzenesulfonate | 6.00 |
| Epoxidized soybean oil | 1.00 |
| Xylene | 39.99 |
| Total | 100.00 |
| Active ingredient | 10.00 |
| Blend of alkylnaphthalenesulfonate and polyoxyethylene ethers | 4.00 |
| Xylene | 86.00 |
| Total | 100.00 |

Flowable formulations are similar to ECs except that the active ingredient is suspended in a liquid carrier, generally water. Flowables, like ECs, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

The following are specific examples of flowable formulations:

| Component: | % by Wt. |
|---|---|
| Active ingredient | 46.00 |
| Colloidal magnesium aluminum silicate | 0.40 |
| Sodium alkylnaphthalenesulfonate | 2.00 |
| Paraformaldehyde | 0.10 |
| Water | 40.70 |
| Propylene glycol | 7.50 |
| Acetylenic alcohols | 2.50 |
| Xanthan gum | 0.80 |
| Total | 100.00 |
| Active ingredient | 45.00 |
| Water | 48.50 |
| Purified smectite clay | 2.00 |
| Xanthan gum | 0.50 |
| Sodium alkylnaphthalenesulfonate | 1.00 |
| Acetylenic alcohols | 3.00 |
| Total | 100.00 |

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acids esters of polyhydric alcohols and the ethylene oxide addition products of such esters; and the addition product of long-chain mercaptans and ethylene oxide. Many other types of useful surface-active agents are available in commerce. The surface-active agent, when used, normally comprises from 1 to 15% by weight of the composition.

Other useful formulations include simple solutions or suspensions of the active ingredient in a relatively non-volatile solvent such as water, corn oil, kerosene, propylene glycol, or other suitable solvents. The following illustrate specific suspensions:

| | % by Wt. |
|---|---|
| Oil Suspension: | |
| Active ingredient | 25.00 |
| polyoxyethylene sorbitol hexaoleate | 5.00 |
| Highly aliphatic hydrocarbon oil | 70.00 |
| Total | 100.00 |
| Aqueous Suspension: | |
| Active ingredient | 40.00 |
| Polyacrylic acid thickener | 0.30 |
| Dodecylphenol polyethylene glycol ether | 0.50 |
| Disodium phosphate | 1.00 |
| Monosodium phosphate | 0.50 |
| Polyvinyl alcohol | 1.00 |
| Water | 56.70 |
| Total | 100.00 |

Other useful formulations for herbicidal applications include simple solutions of the active ingredient in a solvent in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as the Freons, may also be used. Water-soluble or water-dispersible granules are also useful formulations for herbicidal application of the present compounds. Such granular formulations are free-flowing, non-dusty, and readily water-soluble or water-miscible. The soluble or dispersible granular formulations described in U.S. Pat. No. 3,920,442 are useful herein with the present herbicidal compounds. In use by the farmer on the field, the granular formulations, emulsifiable concentrates, flowable concentrates, solutions, etc., may be diluted with water to give a concentration of active ingredient in the range of say 0.1% or 0.2% to 1.5% or 2%.

The active herbicidal compounds of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is of course employed.

The active herbicidal compounds of this invention may be used in combination with other herbicides, e.g. they may be mixed with, say, an equal or larger amount of a known herbicide such as chloroacetanilide herbicides such as 2-chloro-N-(2,6-diethylphenyl)-N-(methoxymethyl)acetamide (alachlor), 2-chloro-N-(2-ethyl-6-methylphenyl)-N-(2-methoxy-1-methylethyl)acetamide (metolachlor), and N-chloroacetyl-N-(2,6-diethylphenyl)glycine (diethatyl-ethyl); benzothiadiazinone herbicides such as 3-(1-methylethyl)-(1H)-2,1,3-benzothiadiazin-4-(3H)-one-2,2-dioxide (bentazon); triazine herbicides such as 6-chloro-N-ethyl-N-(1-methylethyl)-1,3,5-triazine-2,4-diamine (atrazine), and 2-[4-chloro-6-(ethylamino)-1,3,5-triazin-2-yl]amino -2-methylpropanenitrile (cyanazine); dinitrolaniline herbicides such as 2,6-dinitro-N,N-dipropyl-4-(trifluoromethyl)-benzeneamine (trifluralin); and aryl urea herbicides such as N'-(3,4-dichlorophenyl)-N,N-dimethylurea (diuron) and N,N-dimethyl-N'-[3-(trifluoromethyl)phenyl- ]urea (fluometuron); and 2-[(2-chlorophenyl)methyl]-4,4-dimethyl-3-isoxazolidone.

It is apparent that various modifications may be made in the formulation and application of the compounds of this invention without departing from the inventive concepts herein as defined in the claims.

TABLE 1

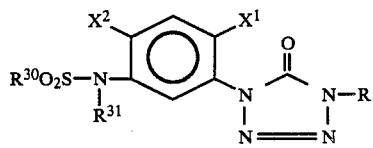

| Cmpd No. | $R^{30}$ | $R^{31}$ | $X^1$ | $X^2$ | R |
|---|---|---|---|---|---|
| 1 | $CH_3$ | H | Cl | Cl | $(CH_2)_2CH_2F$ |
| 2 | $CH_3$ | H | F | Cl | $(CH_2)_2CH_2F$ |
| 3 | $C_2H_5$ | H | Cl | Cl | $(CH_2)_2CH_2F$ |
| 4 | $C_2H_5$ | H | F | Cl | $(CH_2)_2CH_2F$ |
| 5 | $C_3H_7$ | H | Cl | Cl | $(CH_2)_2CH_2F$ |
| 6 | $CH_3$ | $SO_2CH_3$ | H | Cl | $(CH_2)_2CH_2F$ |
| 7 | $CH_3$ | $SO_2CH_3$ | Cl | Cl | $(CH_2)_2CH_2F$ |
| 8 | $CH_3$ | $SO_2CH_3$ | F | F | $(CH_2)_2CH_2F$ |
| 9 | $CH_3$ | $SO_2CH_3$ | F | Cl | $(CH_2)_2CH_2F$ |
| 10 | $CH_3$ | $SO_2CH_3$ | F | Br | $(CH_2)_2CH_2F$ |
| 11 | $CH_3$ | $SO_2CH_3$ | F | Br | $(CH_2)_2CH_2F$ |
| 12 | $C_2H_5$ | $CH_3$ | F | Cl | $(CH_2)_2CH_2F$ |
| 13 | $C_2H_5$ | $C_2H_5$ | F | Cl | $(CH_2)_2CH_2F$ |
| 14 | $C_2H_5$ | $C_3H_7$ | F | Cl | $(CH_2)_2CH_2F$ |
| 15 | $C_2H_5$ | $CH_2OCH_3$ | F | Cl | $(CH_2)_2CH_2F$ |
| 16 | $C_2H_5$ | $CH_2CN$ | F | Cl | $(CH_2)_2CH_2F$ |
| 17 | $C_2H_5$ | $CH_2CO_2H_5$ | F | Cl | $(CH_2)_2CH_2F$ |
| 18 | $C_2H_5$ | $SO_2CO_2H_5$ | H | Cl | $(CH_2)_2CH_2F$ |
| 19 | $C_2H_5$ | $SO_2CO_2H_5$ | Cl | Cl | $(CH_2)_2CH_2F$ |
| 20 | $C_2H_5$ | $SO_2CO_2H_5$ | F | F | $(CH_2)_2CH_2F$ |
| 21 | $C_2H_5$ | $SO_2CO_2H_5$ | F | Cl | $(CH_2)_2CH_2F$ |
| 22 | $C_2H_7$ | $SO_2CO_2H_5$ | F | Br | $(CH_2)_2CH_2F$ |
| 23 | $C_3H_7$ | $SO_2CO_3H_7$ | H | Cl | $(CH_2)_2CH_2F$ |
| 24 | $C_3H_7$ | $SO_2CO_3H_7$ | Cl | Cl | $(CH_2)_2CH_2F$ |
| 25 | $C_3H_7$ | $SO_2CO_3H_7$ | F | F | $(CH_2)_2CH_2F$ |
| 26 | $C_3H_7$ | $SO_2CO_3H_7$ | F | Cl | $(CH_2)_2CH_2F$ |
| 27 | $C_3H_7$ | $SO_2CO_3H_7$ | F | Br | $(CH_2)_2CH_2F$ |
| 28 | $C_3H_7$ | H | F | Cl | $(CH_2)_2CH_2F$ |
| 29 | $C_3H_7$ | $CH_3$ | F | Cl | $(CH_2)_2CH_2F$ |
| 30 | $CF_3$ | H | F | Cl | $(CH_2)_2CH_2F$ |
| 31 | $C_2F_5$ | K | F | Cl | $(CH_2)_2CH_2F$ |
| 32 | $CF_3$ | K | F | Cl | $(CH_2)_2CH_2F$ |
| 33 | $CH_3$ | H | F | Br | $(CH_2)_2CH_2F$ |
| 34 | $C_2H_5$ | H | F | Br | $(CH_2)_2CH_2F$ |
| 35 | $CF_3$ | H | Cl | Cl | $(CH_2)_2CH_2F$ |
| 36 | $CH_3$ | $SO_2CH_3$ | Cl | F | $(CH_2)_2CH_2F$ |
| 37 | $C_2H_5$ | $SO_2C_2H_5$ | Cl | F | $(CH_2)_2CH_2F$ |
| 38 | $CH_3$ | H | Cl | F | $(CH_2)_2CH_2F$ |
| 39 | $C_2H_5$ | H | Cl | F | $(CH_2)_2CH_2F$ |
| 40 | $CH_3$ | $SO_2CH_3$ | F | Cl | $CH_3$ |
| 41 | $C_2H_5$ | $SO_2C_2H_5$ | F | Cl | $CH_3$ |
| 42 | $CH_3$ | H | F | Cl | $CH_3$ |
| 43 | $C_2H_5$ | H | F | Cl | $CH_3$ |
| 44 | $CH_3$ | $SO_2CH_3$ | F | Cl | $C_2H_5$ |
| 45 | $C_2H_5$ | $SO_2C_2H_5$ | F | Cl | $C_2H_5$ |
| 46 | $CH_3$ | H | F | Cl | $C_2H_5$ |
| 47 | $C_2H_5$ | H | F | Cl | $C_2H_5$ |

TABLE 1-continued

| Cmpd No. | $R^{30}$ | $R^{31}$ | $X^1$ | $X^2$ | R |
|---|---|---|---|---|---|
| 48 | $CH_3$ | $SO_2CH_3$ | F | Cl | $C_3H_7$ |
| 49 | $C_2H_5$ | $SO_2C_2H_5$ | F | Cl | $C_3H_7$ |
| 50 | $CH_3$ | H | F | Cl | $C_3H_7$ |
| 51 | $C_2H_5$ | H | F | Cl | $C_3H_7$ |
| 52 | $C_2H_5$ | $SO_2C_2H_5$ | $CH_3$ | $CH_3$ | $(CH_2)_2CH_2F$ |
| 53 | $C_2H_5$ | H | $CH_3$ | $CH_3$ | $(CH_2)_2CH_2F$ |
| 54 | $C_2H_5$ | $CHF_2$ | F | Cl | $(CH_2)_2CH_2F$ |
| 55 | $C_2H_5$ | $CH_2CH_2CH_2F$ | F | Cl | $(CH_2)_2CH_2F$ |
| 56 | $CH(CH_3)_2$ | H | F | Cl | $(CH_2)_2CH_2F$ |
| 57 | $CH(CH_3)_2$ | $SO_2CH(CH_3)_2$ | F | Cl | $(CH_2)_2CH_2F$ |
| 58 | $CH(CH_3)_2$ | H | Cl | Cl | $(CH_2)_2CH_2F$ |
| 59 | $CH(CH_3)_2$ | $SO_2CH(CH_3)_2$ | Cl | Cl | $(CH_2)_2CH_2F$ |
| 60 | $N(CH_3)_2$ | H | F | Cl | $(CH_2)_2CH_2F$ |
| 61 | $N(CH_3)_2$ | H | Cl | Cl | $(CH_2)_2CH_2F$ |
| 62 | $N(C_2H_5)_2$ | H | F | Cl | $(CH_2)_2CH_2F$ |
| 63 | $N(C_2H_5)_2$ | H | Cl | Cl | $(CH_2)_2CH_2F$ |
| 64 | $CH_3$ | $CH(CH_3)_2$ | F | Cl | $(CH_2)_2CH_2F$ |
| 65 | $C_2H_5$ | $CH(CH_3)_2$ | F | Cl | $(CH_2)_2CH_2F$ |
| 66 | $C_2H_5$ | $CH_2COOH$ | F | Cl | $(CH_2)_2CH_2F$ |
| 67 | $CH_3$ | $CH_2COOH$ | F | Cl | $(CH_2)_2CH_2F$ |
| 68 | $CH_3$ | $CH_2C_6H_5$ | F | Cl | $(CH_2)_2CH_2F$ |
| 69 | $CH_3$ | $CH_2C_6H_3Cl_2(2,5)$ | F | Cl | $(CH_2)_2CH_2F$ |
| 70 | $C_2H_5$ | $CH_2C_6H_5$ | F | Cl | $(CH_2)_2CH_2F$ |
| 71 | $CH_3$ | $CH_2CH=CH_2$ | F | Cl | $(CH_2)_2CH_2F$ |
| 72 | $CH_2H_5$ | $CH_2C=CH$ | F | Cl | $(CH_2)_2CH_2F$ |
| 73 | $C_2H_5$ | $OCH_3$ | F | Cl | $(CH_2)_2CH_2F$ |

The compounds in which Z is ethylsulfonylamino, such as compounds 4, 31, 34, have teen found to be particularly useful when used preemergently against broad leaf weeds with crops such as corn, rice, wheat and soybeans. The presence of an N-methylsulfonyl- or N-ethylsulfonylamino group, as in compound 11, gives particularly good results in postemergence use against broadleafed weeds with a favorable selectivity for corn, wheat and soybeans.

Other representative compounds are those which are identical with compounds 5, 11–17, 28–32, 35, 40–51, 54 to 73 respectively except that $X^1$ is F and $X^2$ is Br. Other representative compounds are those which are identical with compounds 1–73 respectively except that $X^1$ is F and $X^2$ is $CF_3$. Still other representative compounds are those which are identical with compounds 1–73 respectively except that $X^1$ is Br.

Compound 4 also shows very good control of broadleaf weeds in plantings of such crops as corn, wheat, barley, oats, rice and sorghum when applied postemergently. Here rates of application in the field may be, for instance, in the range of about 30 to 250 g/ha, e.g., 125 g/ha. 1342W30132Wmd

TABLE 2

| Cmpd No. | Name | Empirical Formula/ m.p. (°C.) | Elemental Analysis | | |
|---|---|---|---|---|---|
| | | | | C | H | N |
| 1 | 1-2[2,4-dichloro-5-(N—methylsulfonyl)-amino]phenyl]-1,4-dihydro-4-(3-fluoropropyl)-5H—tetrazol-5-one | $C_{11}H_{12}Cl_2FN_5O_3S$ Liquid | | | |
| 2 | 1-[4-chloro-2-fluoro-5-(N—methylsulfonylamino)phenyl]-1,4-dihydro-4-(3-fluoropropyl)-5H—tetrazol-5-one | $C_{11}H_{12}ClF_2N_5O_3S$ 106–109 | C F | 35.92 35.69 | 3.29 3.30 | 19.04 18.89 |
| 3 | 1-[2,4-dichloro-5-(N—ethylsulfonylamino)phenyl]-1,4-dihydro-4-(3-fluoropropyl)-5H—tetrazol-5-one | $C_{12}H_{14}Cl_2FN_5O_3S$ 73–73 | C F | 36.20 36.40 | 3.55 3.50 | 17.63 17.50 |
| 4 | 1-[4-chloro-2-fluoro-5-(N—ethyl- | $C_{12}H_{14}ClF_2N_5O_3S$ | C | 37.39 | 3.94 | 18.29 |

TABLE 2-continued

| Cmpd No. | Name | Empirical Formula/ m.p. (°C.) | | Elemental Analysis | | |
|---|---|---|---|---|---|---|
| | | | | C | H | N |
| | sulfonylamino(phenyl]-1,4-dihydro-4-(3-fluoropropyl)-5H—tetrazol-5-one | 84–85 | F | 37.80 | 3.58 | 18.21 |
| 5 | 1-[2,4-dichloro-5-(N—propylsulfonyl-amino)phenyl]-1,4-dihydro-4-(3-fluoropropyl)-5H-tetrazol-5-one | $C_{13}H_{16}Cl_2FN_5O_3S$ Liquid | | | | |
| 6 | 1-[4-chloro-3-]bis(methylsulfonyl)-amino]-1,4-dihydro-4-(3-fluoropropyl)-5H—tetrazol-5-one | $C_{12}H_{15}ClFN_5O_5S_2$ 171–172 | C<br>F | 33.68<br>33.57 | 3.53<br>3.61 | 16.37<br>16.16 |
| 7 | 1-[2,4-dichloro-5-[bis(N—methyl-sulfonyl)amino]phenyl]-1,4-dihydro-4-(3-fluoropropyl)-5H-tetrazol-5-one | $C_{12}H_{14}Cl_2FN_5O_5S_2$ 176–177 | C<br>F | 31.18<br>31.40 | 3.05<br>2.54 | 15.15<br>15.13 |
| 8 | 1-[2,4-difluoro-5-[bis(N—methyl-sulfonyl)amino]phenyl]-1,4-dihydro-4-(3-fluoropropyl)-5H—tetrazol-5-one | $C_{12}H_{14}F_3N_5O_5S_2$ 138–140 | C<br>F | 33.57<br>33.88 | 3.28<br>3.21 | 16.31<br>16.23 |
| 9 | 1-[4-chloro-2-fluoro-5-[bis(N—methyl-sulfonyl(amino]phenyl]-1,4-dihydro-4-(3-fluoropropyl)-5H—tetrazol-5-one | $C_{12}H_{14}ClF_2N_5O_5S_2$ 92–94 | | | | |
| 10 | 1-(4-bromo-2-fluoro-5-[bis(N—methyl-sulfonyl)amino]phenyl]-1,4-dihydro-4-(3-fluoropropyl)-5H—tetrazol-5-one | $C_{12}H_{14}BrF_2N_5O_5S_2$ 143–144 | C<br>F | 29.39<br>29.54 | 2.88<br>2.81 | 14.28<br>14.20 |
| 11 | 1-[4-chloro-2-fluoro-5-[(N—ethyl-sulfonyl-N—methylsulfonyl)amino]-phenyl]-1,4-dihydro-4-(3-fluoro-propyl)-5H—tetrazol-5-one | $C_{13}H_{16}ClF_2N_5O_5S_2$ 124.5–126 | C<br>F | 33.95<br>33.86 | 3.51<br>3.47 | 15.23<br>15.50 |
| 12 | 1-[4-chloro-2-fluoro-5-[(N—ethyl-sulfonyl-N—methyl)amino]phenyl]-1,4-dihydro-4-(3-fluoropropyl)-5H—tetrazol-5-one | $C_{13}H_{16}ClF_2N_5O_5S$ 75–77 | C<br>F | 39.44<br>39.47 | 4.07<br>3.75 | 17.69<br>17.42 |
| 13 | 1-[4-chloro-2-fluoro-5-[(N—ethyl-N—ehtylsulfonyl)amino]phenyl]-1,4-dihydro-4-(3-fluoropropyl)-5H—tetrazol-5-one | $C_{14}H_{18}ClF_2N_5O_3S$ Liquid | C<br>F | 41.02<br>41.72 | 4.42<br>4.54 | 17.09<br>16.21 |
| 14 | 1-[4-chloro-2-fluoro-5-[N—ethyl-sulfonyl-N—propyl)amino]phenyl]-1,4-dihydro-4-(3-fluoropropyl)-5H—tetrazol-5-one | $C_{15}H_{20}ClF_2N_5O_3S$ Liquid | C<br>F | 42.51<br>41.84 | 4.76<br>4.50 | 16.52<br>16.07 |
| 15 | 1-[4-chloro-2-fluoro-5-[(N—ethyl-sulfonyl-N—methoxymethyl)amino]-phenyl]-1,4-dihydro-4-(3-fluoro-propyl)-5H—tetrazol-5-one | $C_{14}H_{18}ClF_2N_5O_4S$ Liquid | C<br>F | 39.49<br>38.71 | 4.26<br>3.97 | 16.44<br>15.48 |
| 16 | 1-[4-chloro-2-fluoro-5-(N—cyano-methyl-N—ethylsulfonyl)amino]phenyl]-1,4-dihydro-4-(3-fluoropropyl)-5H—tetrazol-5-one | $C_{14}H_{15}ClF_2N_6O_3S$ Liquid | C<br>F | 39.95<br>40.16 | 3.59<br>3.54 | 19.97<br>18.03 |
| 17 | ethyl [2-chloro-4-fluoro-5-[1,4-di-hydro-5-oxo-4-(3-fluoropropyl)tetrazol-1-yl]-phenyl(N—ethylsulfonyl)amino]-acetate | $C_{16}H_{20}ClF_2N_5O_5S$ Liquid | C<br>F | 41.07<br>39.41 | 4.30<br>4.45 | 14.96<br>13.54 |
| 18 | 1-[4-chloro-3-[bis(N—ethylsulfonyl)-amino]phenyl]-1,4-dihydro-4-(3-fluoro-propyl)-5H—tetrazol-5-one | $C_{14}H_{19}ClFN_5O_5S_2$ 141–143 | C<br>F | 36.88<br>36.68 | 4.20<br>4.24 | 15.36<br>15.16 |
| 19 | 1-[2,4-dichloro-5-[bis(N—ethylsul-fonyl)amino]phenyl]-1,4-dihydro-4-(3-fluoropropyl)-5H—tetrazol-5-one | $C_{14}H_{18}ClFN_5O_5S_2$ 165–166 | C<br>F | 34.30<br>34.41 | 3.70<br>3.57 | 14.28<br>14.27 |
| 20 | 1-(2,4-difluoro-5-[bis(N—ethylsul-fonyl)amino]phenyl]-1,4-dihydro-4-(3-fluoropropyl)-5H—tetrazol-5-one | $C_{14}H_{18}F_3N_5O_5S_2$ Liquid | C<br>F | 36.76<br>37.02 | 3.96<br>3.85 | 15.31<br>14.79 |
| 21 | 1-[4-chloro-2-fluoro-5-[bis(N—ethyl-sulfonyl)amino]phenyl]-1,4-dihydro-4-(3-fluoropropyl)-5H—tetrazol-5-one | $C_{14}H_{18}ClF_2N_5O_5S_2$ 127–129 | C<br>F | 35.48<br>35.75 | 3.83<br>3.73 | 14.78<br>14.83 |
| 22 | 1-[4-bromo-2-fluoro-5-[bis(N—ehtyl-sulfonyl)amino]phenyl]-1,4-dihydro-4-(3-fluoropropyl)-5H—tetrazol-5-one | $C_{14}H_{18}BrF_2N_5O_5S_2$ 163–164 | C<br>F | 32.44<br>32.63 | 3.50<br>3.53 | 13.51<br>13.51 |
| 23 | 1-[4-chloro-4-[bis(N—propylsulfonyl)-amino[phenyl-1,4-dihydro-4-(3-fluoro-propyl)-5H—tetrazol-5-one | $C_{16}H_{23}ClFN_5O_5S_2$ Liquid | C<br>F | 39.70<br>38.60 | 4.79<br>4.92 | 14.47<br>13.96 |
| 24 | 1-[2,4-dichloro-5-[bis(N—propylsul-fonyl)amino]phenyl]-1,4-dihydro-4-(3-fluoropropyl)-5H—tetrazol-5-one | $C_{16}H_{22}Cl_2FN_5O_5S_2$ 128–129 | C<br>F | 37.08<br>37.09 | 4.27<br>3.90 | 13.51<br>13.43 |
| 25 | 1-[2,4-difluoro-5-[bis(N—propylsul-fonyl(amino]phenyl]-1,4-dihydro-4-(3-fluoropropyl)-5H—tetrazol-5-one | $C_{16}H_{22}F_3N_5O_5S_2$ Liquid | C<br>F | 39.59<br>40.19 | 4.56<br>4.62 | 14.42<br>14.15 |
| 26 | 1-[4-chloro-2-fluoro-5-[bis(N—propyl-sulfonyl)amino]phenyl]-1,4-dihydro-4-(3-fluoropropyl)-5H—tetrazol-5-one | $C_{16}H_{22}ClF_2N_5O_5S_2$ Liquid | C<br>F | 38.29<br>39.41 | 4.42<br>4.54 | 13.95<br>13.83 |
| 27 | 1-[4-bromo-2-fluoro-5-[bis(N—propyl-sulfonyl)amino]phenyl]-1,4-dihydro-4-(3-fluoropropyl)-5H—tetrazol-5-one | $C_{16}H_{22}BrF_2N_5O_5S_2$ 106–107 | C<br>F | 35.17<br>35.83 | 4.06<br>3.90 | 12.81<br>12.62 |
| 28 | 1-[4-Chloro-2-fluoro-5-(N—propyl-sulfonylamino)phenyl]-1,4-dihydro- | $C_{13}H_{16}ClF_2N_5O_3S$ 79–80 | C<br>F | 39.44<br>39.38 | 4.07<br>3.69 | 17.69<br>17.50 |

TABLE 2-continued

| Cmpd No. | Name | Empirical Formula/ m.p. (°C.) | Elemental Analysis | C | H | N |
|---|---|---|---|---|---|---|
| 29 | 4-(3-fluoropropyl)-5H—tetrazol-5-one 1-[4-Chloro-2-fluoro-5-(N—methyl-N—propylsulfonylamino)phenyl]-1,4-dihydro-4-(3-fluoropropyl)-5H—tetrazol-5-one | $C_{14}H_{18}ClF_2N_5O_3S$ liquid | C F | 41.02 41.63 | 4.43 4.52 | 17.09 16.15 |
| 30 | 1-[4-Chloro-2-fluoro-N—trifluoromethyl-sulfonylamino)phenyl]-1,4-dihydro-4-(3-fluoropropyl)-5H—tetrazol-5-one | $C_{11}H_9ClF_5N_5O_3S$ 111–113 | C F | 31.33 31.72 | 2.15 2.24 | 16.60 16.52 |
| 31 | 1-[4-Chloro-2-fluoro-5-(N—ethyl-sulfonylamino)phenyl]-1,4-dihydro-4-(3-fluoropropyl)-5H—tetrazol-5-one potassium salt | $C_{12}H_{13}ClF_2KN_5O_3S$ 100–103 | C F | 34.33 35.76 | 3.12 3.67 | 16.68 16.16 |
| 32 | 1-[4-Chloro-2-fluoro-5-(N—trifluoro-methylsulfonylamino)phenyl]-1,4-dihydro-4-(3-fluoropropyl)-5H—tetrazol-5-one potassium salt | $C_{11}H_8ClF_5KN_5O_3S$ 168–170 | C F | 28.73 28.67 | 1.75 1.78 | 15.23 14.94 |
| 33 | 1-[4-Bromo-2-fluoro-5-(N—methyl-sulfonylamino)phenyl]-1,4-dihydro-(3-fluoropropyl)-5H—tetrazol-5-one | $C_{11}H_{12}BrF_2N_5O_3S$ 113–114 | C F | 32.05 32.11 | 2.94 2.98 | 16.99 16.76 |
| 34 | 1-[4-Bromo-2-fluoro-5-(N—ethyl sulfonylamino)phenyl]-4,5-dihydro- | $C_{12}H_{14}BrF_2N_5O_3S$ 92–94 | C F | 33.82 33.71 | 3.31 3.29 | 16.44 16.18 |
| 35 | 1-[2,4-Dichloro-5-(N—trifluoromethyl-sulfonylamino)phenyl]-4,5-dihydro-4-(3-fluoropropyl)-5H—tetrazol-5-one | $C_{11}H_9Cl_2F_4N_5O_3S$ 137–138 | C F | 30.14 30.77 | 2.07 2.11 | 15.98 15.46 |
| 36 | 1-[2-Chloro-4-fluoro-5-[bis-(N—methylsulfonyl)amino]phenyl]-4,5-dihydro-4-(3-fluoropropyl)-5H—tetrazol-5-one | $C_{12}H_{14}ClF_2N_5O_5S_2$ 175–176 | C F | 32.33 32.28 | 3.16 3.13 | 15.71 15.60 |
| 37 | 1-[2-Chloro-4-fluoro-5-[bis(N—ethylsulfonyl)amino]phenyl]-4,5-dihydro-4-(3-fluoropropyl)-5H—tetrazol-5-one | $C_{14}H_{18}ClF_2N_5O_5S_2$ 148–149 | C F | 35.41 35.46 | 3.82 3.85 | 14.75 14.90 |
| 38 | 1-[2-Chloro-4-fluoro-5-(N—methyl sulfonylamino)phenyl]-4,5-dihydro-4-(3-fluoropropyl)-5H—tetrazol-5-one | $C_{11}H_{12}ClF_2N_5O_3S$ 99–100 | C F | 35.93 35.71 | 3.28 3.22 | 19.04 18.73 |
| 39 | 1-[2-Chloro-4-fluoro-5-(N—ethyl-sulfonylamino)phenyl]-4,5-dihydro-4-(3-fluoropropyl)-5H—tetrazol-5-one | $C_{12}H_{14}ClF_2N_5O_3S$ 91–92 | C F | 37.76 37.61 | 3.69 3.58 | 18.34 18.12 |
| 41 | 1-[4-Chloro-2-fluoro-5-[bis(N—ethylsulfonyl)amino]phenyl]-4,5-dihydro-4-methyl-5H—tetrazol-5-one | $C_{12}H_{15}ClFN_5O_5S_2$ 185–186 | | | | |
| 43 | 1-[4-Chloro-2-fluoro-5-(N—ethyl-sulfonylamino)phenyl]-4,5-dihydro-4-methyl-5H—tetrazol-5-one | $C_{10}H_{11}ClFN_5O_3F$ 158–159 | C F | 35.77 35.90 | 3.30 3.03 | 20.86 20.78 |
| 49 | 1-[4-Chloro-2-fluoro-5-[bis-(N—ethylsulfonyl)amino]phenyl]-4,5-dihydro-4-propyl-5H—tetrazol-5-one | $C_{14}H_{19}ClFN_5O_5S_2$ 134–135 | | | | |
| 51 | 1-[4-Chloro-2-fluoro-5-(N—ethyl-sulfonylamino)phenyl]-4,5-dihydro-4-propyl-5H—tetrazol-5-one | $C_{12}H_{15}ClFN_5O_3S$ 82–83 | C F | 39.61 39.53 | 4.16 4.00 | 19.25 19.16 |

TABLE 3

Preemergence Herbicidal Activity (% Control)

| Compound No. | 2 | 4 | 6 | 8 | 9 | 10 |
|---|---|---|---|---|---|---|
| Rate (kg/ha) | 0.25 | 0.25 | 8.0 | 0.5 | 1.0 | 1.0 |
| Species | | | | | | |
| Cotton | 95 | 95 | 70 | 95 | 100 | 100 |
| Soybean | 20 | 0 | 30 | 30 | 50 | 80 |
| Field Corn | 40 | 30 | 20 | 40 | 100 | 95 |
| Rice | 70 | 40 | | 70 | | 95 |
| Wheat | 10 | 10 | 0 | 10 | 90 | 90 |
| Field Bindweed | 100 | 100 | 20 | 40 | | 100 |
| Morningglory | 100 | 100 | 60 | 60 | 100 | 100 |
| Velvetleaf | 100 | 100 | 95 | 100 | 100 | 100 |
| Barnyardgrass | 60 | 80 | 30 | 40 | 100 | 100 |
| Green Foxtail | 40 | 20 | 30 | 50 | 100 | 100 |
| Johnsongrass | 40 | 30 | 20 | 50 | 80 | 95 |
| Compound No. | 11 | 12 | 13 | 14 | 15 | 16 |
| Rate (kg/ha) | 0.5 | 0.5 | 1.0 | 1.0 | 0.5 | 0.5 |
| Species | | | | | | |
| Cotton | 100 | 100 | 95 | 100 | 100 | 100 |
| Soybean | 30 | 80 | 95 | 95 | 95 | 80 |
| Field Corn | 95 | 100 | 100 | 100 | 100 | 95 |
| Rice | 80 | 90 | 100 | 100 | 100 | 70 |
| Wheat | 80 | 100 | 100 | 100 | 100 | 60 |
| Field Bindweed | 100 | 100 | 100 | 100 | 100 | 100 |
| Morningglory | 100 | 100 | 95 | 100 | 100 | 100 |
| Velvetleaf | 100 | 100 | 100 | 100 | 100 | 100 |
| Barnyardgrass | 100 | 100 | 100 | 100 | 100 | 90 |
| Green Foxtail | 100 | 100 | 100 | 100 | 100 | 100 |
| Johnsongrass | 90 | 100 | 100 | 100 | 100 | 90 |
| Compound No. | 17 | 18 | 20 | 21 | 22 | 23 |
| Rate (kg/ha) | 1.0 | 8.0 | 0.5 | 0.5 | 1.0 | 8.0 |
| Species | | | | | | |
| Cotton | 10 | 100 | 90 | 95 | 100 | 30 |
| Soybean | 10 | 10 | 20 | 20 | 60 | 10 |
| Field Corn | 10 | 0 | 90 | 90 | 95 | 90 |
| Rice | 10 | | 70 | 80 | 80 | 20 |
| Wheat | 20 | 0 | 30 | 95 | 90 | 40 |
| Field Bindweed | 10 | 30 | 20 | | 100 | 70 |
| Morningglory | 30 | 40 | 70 | 95 | 100 | 70 |
| Velvetleaf | 90 | 95 | 100 | 100 | 100 | 100 |
| Barnyardgrass | 20 | 20 | 90 | 100 | 100 | 80 |
| Green Foxtail | 30 | 10 | 95 | 100 | 100 | 95 |
| Johnsongrass | 60 | 40 | 90 | 100 | 100 | 50 |
| Compound No. | 25 | 26 | 27 | 28 | 29 | 30 |
| Rate (kg/ha) | 0.5 | 0.500 | 1.0 | 0.5 | 0.25 | 0.25 |

TABLE 3-continued

| Species | | | | | | |
|---|---|---|---|---|---|---|
| Cotton | 10 | 50 | 95 | 100 | 60 | 50 |
| Soybean | 20 | 0 | 30 | 0 | 30 | 10 |
| Field Corn | 80 | 90 | 95 | 30 | 95 | 10 |
| Rice | 20 | 20 | 60 | 70 | 60 | 20 |
| Wheat | 20 | 60 | 60 | 30 | 80 | 0 |
| Field Bindweed | 0 | | 100 | 100 | 70 | 95 |
| Morningglory | 10 | 60 | 100 | 100 | 70 | 60 |
| Velvetleaf | 20 | 100 | 100 | 100 | 100 | 100 |
| Barnyardgrass | 50 | 100 | 100 | 95 | 100 | 0 |
| Green Foxtail | 10 | 60 | 100 | 90 | 100 | 10 |
| Johnsongrass | 60 | 95 | 95 | 70 | 100 | 60 |
| Compound No. | 31 | 32 | 33 | 34 | 35 | 36 |
| Rate (kg/ha) | 0.25 | 2.0 | 0.25 | 0.25 | 4.0 | 2.0 |
| Species | | | | | | |
| Cotton | 100 | 100 | 100 | 95 | 100 | 70 |
| Soybean | 10 | 40 | 10 | 20 | 80 | 0 |
| Field Corn | 30 | 50 | 40 | 60 | 50 | 70 |
| Rice | 40 | 95 | 80 | 60 | 95 | 0 |
| Wheat | 20 | 10 | 20 | 0 | 70 | 0 |
| Field Bindweed | 100 | 100 | 100 | 100 | 100 | 100 |
| Morningglory | 100 | 100 | 100 | 100 | 100 | 90 |
| Velvetleaf | 100 | 100 | 100 | 100 | 100 | 95 |
| Barnyardgrass | 95 | 95 | 95 | 95 | 90 | 70 |
| Green Foxtail | 50 | 60 | 70 | 70 | 100 | 50 |
| Johnsongrass | 70 | 80 | 70 | 50 | 95 | 40 |
| Compound No. | 37 | 38 | 39 | 40 | 41 | 49 | 51 |
| Rate (kg/ha) | 2.0 | 1.0 | 1.0 | 4.0 | 2.0 | 2.0 | 2.0 |
| Species | | | | | | | |
| Cotton | 10 | 70 | 50 | 50 | 95 | 90 | 100 |
| Soybean | 0 | 50 | 10 | 20 | 50 | 20 | 20 |
| Field Corn | 20 | 10 | 70 | 30 | 40 | 90 | 70 |
| Rice | 0 | 40 | 10 | 20 | 10 | 70 | 30 |
| Wheat | 30 | 10 | 20 | 30 | 10 | 95 | 20 |
| Field Bindweed | 20 | 95 | 70 | 40 | 100 | 80 | 100 |
| Morningglory | 20 | 100 | 100 | 70 | 100 | 70 | 100 |
| Velvetleaf | 100 | 100 | 100 | 100 | 100 | 100 | 100 |
| Barnyardgrass | 80 | 80 | 60 | 70 | 80 | 100 | 70 |
| Green Foxtail | 50 | 80 | 50 | 40 | 95 | 100 | 95 |
| Johnsongrass | 70 | 40 | 10 | 40 | 20 | 80 | 10 |

TABLE 4

Postemergence Herbicidal Activity (% Control)

| Compound No. | 2 | 4 | 6 | 8 | 9 | 10 |
|---|---|---|---|---|---|---|
| Rate (kg/ha) | 0.25 | 0.25 | 8.0 | 0.5 | 1.0 | 1.0 |
| Species | | | | | | |
| Cotton | 100 | 100 | 90 | 95 | 100 | 100 |
| Soybean | 50 | 60 | 50 | 40 | 30 | 95 |
| Field Corn | 80 | 50 | 40 | 50 | 30 | 90 |
| Rice | 50 | 20 | 30 | 20 | | 30 |
| Wheat | 20 | 20 | 20 | 30 | 80 | 60 |
| Field Bindweed | 100 | 100 | 70 | 30 | | 100 |
| Morningglory | 100 | 95 | 100 | 40 | 100 | 100 |
| Velvetleaf | 100 | 100 | 100 | 95 | 100 | 100 |
| Barnyardgrass | 40 | 50 | 50 | 40 | 100 | 100 |
| Green Foxtail | 50 | 80 | 50 | 50 | 60 | 100 |
| Johnsongrass | 50 | 20 | 20 | 30 | 70 | 100 |
| Compound No. | 11 | 12 | 13 | 14 | 15 | 16 |
| Rate (kg/ha) | 0.5 | 0.5 | 1.0 | 1.0 | 0.5 | 0.5 |
| Species | | | | | | |
| Cotton | 100 | 100 | 100 | 100 | 100 | 100 |
| Soybean | 60 | 70 | 95 | 100 | 95 | 70 |
| Field Corn | 80 | 70 | 100 | 100 | 95 | 50 |
| Rice | 40 | 30 | 100 | 100 | 60 | 50 |
| Wheat | 70 | 80 | 100 | 100 | 100 | 60 |
| Field Bindweed | 100 | 100 | 100 | 100 | 80 | 100 |
| Morningglory | 80 | 100 | 100 | 100 | 100 | 100 |
| Velvetleaf | 100 | 100 | 100 | 100 | 100 | 100 |
| Barnyardgrass | 80 | 70 | 100 | 100 | 80 | 50 |
| Green Foxtail | 80 | 70 | 100 | 100 | 90 | 70 |

TABLE 4-continued

| Johnsongrass | 50 | 70 | 100 | 100 | 80 | 60 |
|---|---|---|---|---|---|---|
| Compound No. | 17 | 18 | 20 | 22 | 23 | 25 |
| Rate (kg/ha) | 1.0 | 8.0 | 0.5 | 1.0 | 8.0 | 0.5 |
| Species | | | | | | |
| Cotton | 90 | 60 | 90 | 100 | 60 | 40 |
| Soybean | 50 | 60 | 30 | 95 | 40 | 20 |
| Field Corn | 60 | 30 | 20 | 100 | 30 | 60 |
| Rice | 20 | | 20 | 80 | | 20 |
| Wheat | 40 | 10 | 50 | 90 | 20 | 20 |
| Field Bindweed | 80 | 50 | 30 | 95 | 50 | 40 |
| Morningglory | 60 | 70 | 90 | 95 | 60 | 30 |
| Velvetleaf | 95 | 95 | 100 | 100 | 100 | 80 |
| Barnyardgrass | 40 | 30 | 30 | 100 | 40 | 20 |
| Green Foxtail | 40 | 30 | 40 | 100 | 40 | 30 |
| Johnsongrass | 40 | 30 | 30 | 100 | 40 | 20 |
| Compound | 26 | 27 | 28 | 29 | 30 | 31 |
| Rates (kg/ha) | 0.5 | 1.0 | 0.5 | 0.25 | 0.25 | 0.25 |
| Species | | | | | | |
| Cotton | 100 | 100 | 100 | 70 | 90 | 100 |
| Soybean | 50 | 90 | 30 | 70 | 40 | 80 |
| Field Corn | 100 | 95 | 40 | 40 | 30 | 30 |
| Rice | 40 | 30 | 70 | 60 | 10 | 40 |
| Wheat | 90 | 80 | 60 | 80 | 10 | 40 |
| Field Bindweed | | 95 | 100 | 80 | 70 | 100 |
| Morningglory | 100 | 100 | 100 | 70 | 80 | 100 |
| Velvetleaf | 100 | 100 | 100 | 100 | 100 | |
| Barnyardgrass | 80 | 100 | 100 | 50 | 10 | 80 |
| Green Foxtail | 80 | 100 | 100 | 60 | 0 | 60 |
| Johnsongrass | 70 | 100 | 95 | 70 | 0 | 60 |
| Compound No. | 32 | 33 | 34 | 35 | 36 | 37 |
| Rate (kg/ha) | 2.0 | 0.25 | 0.25 | 4.0 | 2.0 | 2.0 |
| Species | | | | | | |
| Cotton | 100 | 100 | 100 | 100 | 70 | 70 |
| Soybean | 100 | 70 | 70 | 100 | 10 | 40 |
| Field Corn | 70 | 30 | 40 | 70 | 10 | 20 |
| Rice | 40 | 80 | 70 | 80 | 10 | 20 |
| Wheat | 40 | 40 | 40 | 40 | 10 | 20 |
| Field Bindweed | 100 | 100 | 100 | 95 | 60 | 40 |
| Morningglory | 100 | 100 | 100 | 100 | 80 | 50 |
| Velvetleaf | 100 | 100 | 100 | 100 | 90 | 80 |
| Barnyardgrass | 70 | 80 | 70 | 70 | 50 | 30 |
| Green Foxtail | 40 | 100 | 90 | 100 | 50 | 50 |
| Johnsongrass | 70 | 70 | 50 | 90 | 50 | 20 |
| Compound No. | 38 | 39 | 40 | 43 | 49 | 51 |
| Rate (kg/ha) | 1.0 | 1.0 | 4.0 | 2.0 | 2.0 | 2.0 |
| Species | | | | | | |
| Cotton | 95 | 100 | 40 | 100 | 100 | 100 |
| Soybean | 90 | 95 | 20 | 50 | 50 | 70 |
| Field Corn | 50 | 50 | 20 | 30 | 80 | 60 |
| Rice | 20 | 20 | 10 | 50 | 50 | 60 |
| Wheat | 50 | 30 | 20 | 50 | 80 | 70 |
| Field Bindweed | 100 | 100 | 40 | 100 | 80 | 100 |
| Morningglory | 100 | 100 | 60 | 100 | 90 | 100 |
| Velvetleaf | 100 | 100 | 70 | 95 | 100 | 100 |
| Barnyardgrass | 50 | 50 | 60 | 50 | 95 | 80 |
| Green Foxtail | 80 | 50 | 30 | 40 | 95 | 80 |
| Johnsongrass | 80 | 50 | 30 | 70 | 90 | 70 |

I claim:
1. A compound of the formula

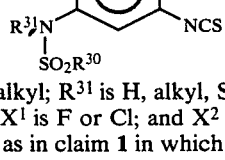

in which $R^{30}$ is alkyl; $R^{31}$ is H, alkyl, $SO_2R^{30}$, or a salt-forming cation; $X^1$ is F or Cl; and $X^2$ is Cl or Br.

2. Compound as in claim 1 in which $X^1$ is F, $X^2$ is Cl, $R^{31}$ is H, $R^{30}$ is ethyl.

* * * * *